United States Patent
Makarov

(10) Patent No.: US 9,043,164 B2
(45) Date of Patent: May 26, 2015

(54) METHOD OF GENERATING A MASS SPECTRUM HAVING IMPROVED RESOLVING POWER

(75) Inventor: Alexander Alekseevich Makarov, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 790 days.

(21) Appl. No.: 13/278,015

(22) Filed: Oct. 20, 2011

(65) Prior Publication Data
US 2012/0109537 A1    May 3, 2012

(30) Foreign Application Priority Data
Nov. 2, 2010 (EP) .................................. 10189667

(51) Int. Cl.
G06F 19/00 (2011.01)
H01J 49/00 (2006.01)
H01J 49/38 (2006.01)
H01J 49/02 (2006.01)

(52) U.S. Cl.
CPC ........... H01J 49/0036 (2013.01); H01J 49/027 (2013.01); G06F 19/70 (2013.01); H01J 49/38 (2013.01)

(58) Field of Classification Search
CPC ..... H01J 49/0036; H01J 49/027; H01J 49/38; G06F 19/70
USPC .......................................................... 702/27
See application file for complete search history.

(56) References Cited

U.S. PATENT DOCUMENTS

| 4,978,852 A * | 12/1990 | Williams et al. ............... 250/282 |
| 7,495,209 B2 * | 2/2009 | Baykut et al. .................. 250/282 |
| 2005/0118650 A1 * | 6/2005 | Dasseux et al. ................. 435/7.2 |

(Continued)

FOREIGN PATENT DOCUMENTS

| WO | WO 2005/031791 | 4/2005 |
| WO | WO 2007/014035 | 12/2007 |
| WO | WO 2008/008867 | 1/2008 |

OTHER PUBLICATIONS

Scigelova et al., "Fourier Transform Mass Spectrometry" Mol Cell Proteomics. Jul. 2011; 10(7): M111.009431, published online May 9, 2011.*

(Continued)

Primary Examiner — Mohamed Charioui
Assistant Examiner — John Kuan
(74) Attorney, Agent, or Firm — David A. Schell; Charles B. Katz

(57) ABSTRACT

A method is disclosed for generating a mass spectrum, e.g. for Fourier transform mass spectrometry, having improved resolving power. The method includes steps of acquiring a plurality of mass spectra from a mass spectrometer using image current detection determining the centroids of at least some of the peaks which have a sufficient signal-to-noise (S/N) ratio so that the variation of the centroid of each such peak from the plurality of mass spectra is significantly lower than the full-width at half-maximum, dM, of the peak in the m/z domain; and generating a histogram of the centroids determined from the plurality of acquired mass spectra thereby forming a composite mass spectrum. The resultant composite mass spectrum comprises peaks having full-width at half-maximum, dMC, significantly narrower than the peak width, dM, of the corresponding peaks in the plurality of acquired mass spectra.

16 Claims, 8 Drawing Sheets

(56) References Cited

U.S. PATENT DOCUMENTS

2007/0176091 A1* 8/2007 Lange et al. ............. 250/288
2008/0029697 A1* 2/2008 Willis et al. ............. 250/287
2008/0203288 A1* 8/2008 Makarov et al. .......... 250/282
2008/0270083 A1* 10/2008 Lange et al. ............. 702/193
2009/0206247 A1* 8/2009 Holle ...................... 250/282
2011/0240841 A1* 10/2011 Lange ..................... 250/282

OTHER PUBLICATIONS

Hu et al., "The Orbitrap: a new mass spectrometer" Journal of Mass Spectrometry 2005; 40: 430-443.*

A. Makarov, "Electrostatic Axially Harmonic Orbital Trapping: A High-Performance Technique of Mass Analysis" Anal. Chem. 2000, 72, 1156-1162.*

Makarov et al., "Performance Evaluation of a Hybrid Linear Ion Trap/Orbitrap Mass Spectrometer" Analytical Chemistry, vol. 78, No. 7, 2113-2120, Apr. 1, 2006.*

Makarov et al., "Dynamic Range of Mass Accuracy in LTQ Orbitrap Hybrid Mass Spectrometer" J Am Soc Mass Spectrom 2006, 17, 977-982; published online Jun. 5, 2006.*

* cited by examiner

METHOD OF GENERATING A MASS SPECTRUM HAVING IMPROVED RESOLVING POWER

CROSS-REFERENCE TO RELATED APPLICATION

This application claims the priority benefit of European Patent Application No. 10189667.8, filed Nov. 2, 2010, which application is incorporated herein by reference in its entirety.

FIELD OF THE INVENTION

This invention relates to a method of generating a mass spectrum. The method is useful for a mass spectrometer employing image current detection of ions. The invention may be used for the production of high resolving power mass spectra and these spectra may be used for the identification and/or quantification of organic compounds, e.g. macromolecules and active pharmacological ingredients, metabolites, small peptides and/or proteins.

BACKGROUND OF THE INVENTION

Mass spectrometers are widely used to separate and analyse ions on the basis of their mass to charge ratio (m/z). For certain types of mass spectrometer which acquire data in the form of a transient, for example by detection of an induced oscillating image current, the use of Fourier transforms (FT) is a well known and established data processing technique enabling high resolution mass spectra to be obtained from mass spectrometers. Various other transforms may be used but Fourier transforms are by far the most widely used due to their relative high speed and simplicity. Description of the FT technique can be found, for example, in Marshall, A. G. & Verdun, F. R., *Fourier Transforms in NMR, Optical and Mass Spectrometry; A User's Handbook*, Elsevier, 1990. Examples of FT mass spectrometers include Fourier transform ion cyclotron resonance (FT-ICR) mass spectrometers and ion traps that measure the frequency of ion oscillation induced by an electrostatic potential that varies harmonically in one direction such as the Orbitrap™ mass spectrometer from Thermo Fisher Scientific (herein referred to as harmonic potential-FTMS).

In the aforesaid types of FT mass spectrometer the ions being analysed are urged to undergo oscillatory motion within the spectrometer which induces a correspondingly oscillatory image charge in neighbouring detection electrodes which enables detection of the ions. The oscillatory motion may be of various forms including, for example, circular oscillatory motion in the case of FT-ICR and axial oscillatory motion whilst orbiting about a central electrode in the case of certain harmonic potential-FTMS such as an Orbitrap™ MS. The oscillatory image charge in turn induces an oscillatory image current in circuitry connected to the detection electrodes, which is then typically amplified, digitised and received by a processor such as a computer as a transient (i.e. a signal in the time domain). The oscillating ions induce oscillatory image current at frequencies which are related to the mass-to-charge (m/z) values of the ions. Each ion of a given mass to charge (m/z) value will oscillate at a corresponding given frequency such that it contributes a signal to the transient which is generally in the form of a sine-shaped wave at the given frequency. The total detected image current of the transient is then the resultant sum of the image currents at all the frequencies present (i.e. a sum of sine waves signals). Fourier transformation of the transient yields the oscillation frequencies associated with the particular detected oscillating ions and from the frequencies the m/z values of the ions can be determined (i.e. the mass spectrum) by known equations.

For all types of mass spectrometry there is a desire to improve the resolving power of the instrument. For example, a method to counter peak broadening due to the detector in time-of-flight MS is disclosed in US 2003/0218129 A1.

Various methods exist to increase the resolving power of mass spectrometry employing image current detection of oscillating ions such as Fourier transform mass spectrometry (FTMS). Probably the best known method is to increase the detection time. If the transient signal itself has sufficient duration a doubling of the detection time doubles the resolving power of the system. However, FTMS requires relatively long detection times to achieve high resolving powers. This method of increasing the resolving power by increasing detection time has potential drawbacks, such as signal decay over time (e.g. due to de-phasing, or ion loss by collisions) which limits the maximum achievable resolution. The signal may also deteriorate over time, e.g. due to frequency drift, further limiting the maximum achievable resolution or resolving power. Some of these effects are now described in more detail.

An increase of resolving power of m/z analysis in FTMS by extension of the detection time requires acquiring longer transients of image current induced on the detection electrodes by coherent oscillations of ion packets. However, the coherency of an ion packet or even its very existence cannot always be supported for a long time. This is especially true for analysis of intact proteins which can suffer rapid decay in FT mass spectrometers because of collisions with residual gas and sometimes metastable fragmentation. The higher the mass of proteins, the more resolving power is required to resolve its C-13 isotopes and frequently the faster is the decay of such proteins in FTMS (primarily due to collisions). At present this limits the mass of the highest isotopically resolvable protein to approx. 110 kDa for FT-ICR and 70 kDa for an Orbitrap MS. At the same time, increasing pharmaceutical importance of heavier proteins (such as antibodies with MW around 150 kDa) emphasizes the need for more comprehensive and accurate analysis of these proteins and their modifications. The ability to resolve isotopically these forms would greatly increase reliability of identification of such modifications. It is thus desirable to further increase the resolving power for a given detection or acquisition time.

However, there exist obstacles to the improvement of resolving power for a given detection or acquisition time. Technical solutions like, e.g., increase of the magnetic field in FT-ICR-MS or changes to the field geometry and voltages of an Orbitrap™ MS, may be difficult or prohibitively expensive.

For a given signal the resolution or resolving power can be improved by various well known mathematical methods, such as: (i) Linear prediction, Autocorrelation and/or maximum entropy methods [see Marshall, A. G. & Verdun, F. R., *Fourier Transforms in NMR, Optical and Mass Spectrometry; A User's Handbook*, Elsevier, 1990, chapter 6], which all require major software development and have not yet been routinely used in FTMS due to their high computational expense when compared with the expected resolution gains; (ii) display in absorption mode [see Marshall, A. G. & Verdun, F. R., *Fourier Transforms in NMR, Optical and Mass Spectrometry; A User's Handbook*, Elsevier, 1990, chapter 2.4.2]; and (iii) FSD (Fourier self deconvolution) if resolution is limited by other factors than detection time, and Peak fitting, i.e. involving fitting multiple model peaks to one real peak, both of which usually require an a priori knowledge of the peak shape. Moreover, the aforementioned mathematical methods typically promise only moderate increases of resolution or resolving power (e.g. about 2 to 3 times) although most of the aforementioned techniques can be utilised together with the present invention as will be apparent below.

A totally different technical approach is to detect the flight time of ions ejected from an FT-ICR cell after resonant excitation and infer the exact mass from small differences in the flight time induced by the cyclotron resonance [see Becker, S.; Bollen, G.; Kern, F.; Kluge, H.-J.; Moore, R. B.; Savard, G.; Schweikhard, L. & Stolzenberg, H.: Mass Measurements of Very High Accuracy by Time-Of-Flight Ion Cyclotron Resonance of Ions Injected into a Penning Trap; *International Journal of Mass Spectrometry and Ion Processes*, 1990, 99, 53-77]. This indirect measurement by ion ejection is currently only proven for FT-ICR and used in heavy isotope research because it is very fast (no necessity for transient detection).

Accordingly, there remains a need to improve the resolving power in mass spectrometry, especially for mass spectrometry using image current detection. In view of the above background, the present invention has been made.

SUMMARY OF THE INVENTION

According to an aspect of the present invention there is provided a method of generating a mass spectrum, comprising:
  acquiring a plurality of mass spectra from a mass spectrometer using image current detection wherein most of the peaks are due to the detection of individual ions;
  determining the centroids of at least some of the peaks which are due to the individual ions and which have a sufficient signal-to-noise (S/N) ratio so that the variation of the centroid of each such peak from the plurality of mass spectra is significantly lower than the full-width at half-maximum, dM, of the peak in the m/z domain; and
  generating a histogram of the centroids determined from the plurality of acquired mass spectra thereby forming a composite mass spectrum wherein the composite mass spectrum comprises peaks and the full-width at half-maximum, dMC, of these peaks in the m/z domain is significantly narrower than the peak width, dM, of the corresponding peak in the plurality of acquired mass spectra.

According to another aspect of the present invention there is provided a method of generating a mass spectrum, comprising:
  acquiring a plurality of mass spectra from a mass spectrometer using image current detection wherein the probability of simultaneously detecting in a single spectrum any two ions giving rise to overlapping peaks in the m/z domain is significantly lower than the probability of detecting either of the two ions alone;
  determining the centroids of at least some peaks in the plurality of mass spectra which have a sufficient signal-to-noise (S/N) ratio so that the variation of the centroid of each such peak from the plurality of mass spectra is significantly lower than the full-width at half-maximum dM of the peak in the m/z domain; and
  generating a histogram of the centroids determined from the plurality of acquired mass spectra thereby forming a composite mass spectrum wherein the composite mass spectrum comprises peaks and the full-width at half-maximum dMC of these peaks in the m/z domain is significantly narrower than the peak width dM of the corresponding peak in the plurality of acquired mass spectra.

According to a further aspect of the present invention there is provided a method of improving the resolving power of mass spectrometric analysis of ion peaks closely separated in m/z domain, comprising:
  detecting ions in a mass spectrometer using image current detection to provide ion signals representing the abundance of the ions in the mass spectrometer;
  adjusting the intensity of the ion signals by adjusting the number of ions in the mass spectrometer so that the probability of simultaneously detecting in a single spectrum any two ions giving rise to overlapping peaks in the m/z domain is significantly lower than the probability of detecting either of the ions alone;
  acquiring a plurality of mass spectra from the mass spectrometer after said adjusting of the ion signals;
  determining the centroids of at least some peaks in the acquired mass spectra, wherein the variation of the centroid of each such peak from the plurality of mass spectra is significantly lower than the full-width at half-maximum of the peak dM in the m/z domain; and
  generating a histogram of the centroids determined from the plurality of acquired mass spectra thereby forming a composite mass spectrum.

According to a still another aspect of the present invention there is provided a method of generating a mass spectrum, comprising:
  acquiring a plurality of mass spectra from a mass spectrometer using image current detection wherein most of the peaks are due to the detection of individual ions;
  determining the centroids of at least some of the peaks which are due to the individual ions and which have a sufficient signal-to-noise (S/N) ratio so that the variation of the centroid of each such peak from the plurality of mass spectra is significantly lower than the full-width at half-maximum dM of the peak in the m/z domain; and
  generating a histogram of the centroids determined from the plurality of acquired mass spectra thereby forming a composite mass spectrum.

The present invention provides a method of improving the resolving power and enables the resolving power of a mass spectrometer employing image current detection, such as FTMS, to be increased beyond the limits imposed by the duration of the image current signal. The composite mass spectrum formed by the histogram of the centroids has a significantly higher resolving power than the acquired mass spectra immediately after transformation of the image current signal from the time domain. Moreover, the invention may be implemented with relatively low computational effort. The resolving power in a mass spectrum is defined as the observed mass (m) divided by the difference between two masses ($\Delta m$) that can be separated, i.e. m/$\Delta m$.

The invention in one aspect comprises acquiring a plurality of mass spectra from a mass spectrometer using image current detection wherein most of the peaks are due to the detection of individual ions as described in more detail hereafter. In another aspect the invention comprises acquiring a plurality of mass spectra from a mass spectrometer using image current detection wherein the probability of simultaneously detecting in a single spectrum any two ions giving rise to overlapping peaks in the m/z domain is significantly lower than the probability of detecting either of the ions alone as described in more detail hereafter and in that aspect at least some of the peaks are due to the detection of individual ions (preferably most of the peaks are due to the detection of individual ions).

For each data acquisition, the image current detection initially comprises generating a transient (time domain signal) from the oscillation of ions in the spectrometer, which is then transformed into the frequency domain by a transformation which is typically a Fourier transformation (giving a Fourier transformed spectrum) because such transformations are fast but may be another transformation such as Hadamard, wavelet and others. The methods for image current detection and transformation of the transient into the frequency domain are well known in the art. The frequency domain spectrum may be converted into the m/z domain, again by well known methods.

In this description, any spectrum in the mass domain or a domain related thereto, such as the m/z domain or frequency domain for example, is referred to as a mass spectrum. Correspondingly, references herein to mass also refer to quantities or parameters related thereto, such as m/z or frequency for example.

In the present invention, the mass spectra are preferably acquired with a mass precision of the peaks which is better (i.e. narrower) than the mass separation between adjacent peaks, e.g. between adjacent isotopes of an analyte. The mass precision is the variation of the measured mass, i.e. the variation of the centroid value, during the acquisition of the plurality of mass spectra for creation of the histogram. Most preferably, the mass precision of the peaks in the acquired mass spectra is at most 0.2, especially at most 0.1, times the peak width dM of the peaks in the acquired mass spectra (i.e. the Fourier transformed mass spectra). The mass precision of the peaks with high signal-to-noise ratio in the acquired mass spectra is typically 1 ppm or less, e.g. in the range 100 ppb to 1 ppm or 30 ppb to 1 ppm. The mass accuracy on the other hand is the measure of the correctness of the measured mass, i.e. its closeness to the true mass of the ion. The mass accuracy of the peaks in the acquired mass spectra is typically 5 ppm or less, more typically between 1 ppm and 5 ppm, more preferably 2 ppm or less and most preferably 1 ppm or less. The mass precision in FTMS is related to the S/N ratio and thus a sufficiently high S/N ratio needed to be provided when detecting individual ions. The centre of a peak obtained in FTMS can be determined with a precision $dC=(FWHM/2)/(SN*\sqrt{K})$, where FWHM is the full width of the peak at half the maximum peak height and FWHM in the mass domain is approximately equal to 2*r.m.s. of mass deviation; SN is the S/N ratio of the peak; and K is the number of samples (data points) across the peak (typically 5). Further details of this relationship are given in L. Chen, C. E. Cottrell and A. G. Marshall *Effect of Signal-to-Noise Ratio and Number of Data Points upon Precision in Measurement of Peak Amplitude, Position and Width in Fourier Transform Spectrometry*, Chemometrics and Intelligent Laboratory Systems, 1 (1986) 51-58. For example, for a nominal spectrometer resolution of 30,000, dC=10 ppm/SN. Image current detection methods known in the art are capable of detecting individual ions with sufficiently high S/N (preferably S/N greater than 1, more preferably greater than 2, greater than 3, greater than 4 and even more preferably greater than 5) that high mass precision is obtained. The peaks in the acquired mass spectra which may be used for centroiding have a sufficiently high signal-to-noise (S/N) ratio so that the variation of the centroid for a peak from the plurality of mass spectra is significantly lower than its full-width at half-maximum (FWHM) dM in the m/z domain, preferably less than 0.5 times dM, more preferably less than 0.4 times dM, still more preferably less than 0.3 times dM and most preferably less than 0.2 times dM, especially less than 0.1 times dM.

The sufficiently high mass precision of the acquired spectra means that ions present at different times (i.e. in different spectra or scans) can be differentiated by their peak position (i.e. mass, m/z or frequency). By using low numbers of ions in the spectrometer this high mass precision is used to enable a plurality of acquired spectra to be used to form a composite mass spectrum in which the peaks are present together but resolved.

The mass spectra obtained after Fourier transformation (or other appropriate transformation) are used to determine centroids of at least some of the peaks in the spectra. Only the centroids, and optionally further data relating to the peak intensity, are then used for subsequent processing.

When during detection the probability of two peaks overlapping is low, such as happens when the conditions in the spectrometer are such that most of the peaks found in a mass spectrum are due to individual ions, the measured centroid indicates quite accurately and precisely (e.g. within a few ppm or even a few ppb) the (mass or frequency) position of the ion, e.g. the corresponding isotope of analyte. When this factor is coupled with the high mass precision of the image current detection method, a histogram or distribution of centroids on mass generated after acquiring a sufficient number of mass spectra, enables an improvement in resolving power to be achieved, e.g. using a data group width in the histogram significantly smaller than the data group width of the original transformed mass spectra. In other words, after acquiring a sufficiently large number of mass spectra, and determining the centroids from the spectra, the histogram of centroids will start to approximate the real mass spectrum of the analyte but with improved resolving power.

Preferably, the composite mass spectrum comprises peaks and the full-width at half-maximum dMC of these peaks in the m/z domain is at least X times narrower than the peak width dM of the corresponding peak in the plurality of acquired mass spectra, wherein X is 2. Preferably X is 3, 4, 5, 6, 7, 8, 9, 10 or more. Accordingly, especially, the full-width at half-maximum dMC of the peaks in the composite spectrum in the m/z domain is at least 3 times narrower than the peak width dM, more especially at least 4 times narrower, still more especially at least 5 times narrower and most especially at least 10 times narrower.

Preferably, the centroids are collected in the histogram in data groups which are narrower in width than the FWHM peak width dM of the peaks in the acquired mass spectra. Further preferably, the centroids are collected in the histogram in data groups which are narrower in width than the FWHM peak width dMC of the peaks in the composite mass spectrum. Preferably, the centroids are collected in the histogram in data groups which are at least X times narrower in width than the peak width, dM, wherein X is 2. Preferably X is 3, 4, 5, 6, 7, 8, 9, 10 or more. The data groups can be located in any position in the histogram and of such width provided that they do not overlap. The location of a data group could be for example the average mass of the centroids collected in it. The data groups can be data bins of uniform width and/or spacing (e.g. located next to one another). Alternatively, the data groups can be of flexible width and/or spacing and thus need not be adjacent to one another.

Preferably, the data group width of the histogram is at least X times narrower than the data group width of the acquired mass spectra in the m/z domain (i.e. after transformation), wherein X is defined as above (thus preferably X is 2, more preferably 3, still more preferably 4 and most preferably 5).

Preferably a sufficient number of mass spectra are acquired such that the histogram of the centroids determined from the mass spectra will approximate the real mass spectrum of the analyte. Preferably at least 10, more preferably at least 100 and most preferably at least 1000 (typically many thousands, even 10,000 or more) spectra are acquired to form the histogram. The acquisition of 10,000 spectra typically takes above 2 hours at a pace of 1 spectra per second. Such a histogram thus constitutes a synthetic or composite spectrum which may have a much higher resolution or resolving power than the "raw" resolving power of the original acquisition, e.g. of the Fourier transformed spectrum. With the use of present invention, from the histogram the mass position of a peak may be determined to 0.5, or 0.2, or 0.1, or even less, of the data group width of the Fourier-transformed spectrum. This can be achieved by using a data group width in the histogram which is at least 2 times narrower than the data group width of the acquired mass spectra in the m/z domain. Preferably (in order of increasing preference), the data group width in the histogram is at least 3 times, at least 4 times, at least 5 times, at least 6 times, at least 7 times, at least 8 times, at least 9 times, at least 10 times, narrower than the data group width of the acquired mass spectra in the m/z domain. Practically, an improvement in resolving power of 3-6 times or greater can be readily achieved using the present invention, the improvement being greater for higher signal-to-noise ratios of the peaks and longer detection times.

It should be understood that herein the term histogram means a generalised histogram and therefore includes histograms consisting of a series of data groups as described above, but also (of which a normal histogram is a special case). Kernel density estimates are described, for example, at http://en.wikipedia.org/wiki/Kernel_density_estimation.

The resulting composite mass spectrum constructed from the histogram may then be used for subsequent processing in known ways, e.g. deconvolution by software, in order to estimate monoisotopic mass of the protein and its modified forms.

As already mentioned, the present invention uses image current detection of oscillating ions in the spectrometer to acquire mass spectra of the ions. Modern image current detection electronics is capable of detecting individual ions, especially when such ions carry multiple charges and when duration of detection is long enough (e.g. 0.5-2.0 seconds) as shown by A. A. Makarov, E. Denisov. "Dynamics of ions of intact proteins in the Orbitrap mass analyzer". *J. Am. Soc. Mass Spectrom.* 2009, 20, 1486-1495. As heavy proteins are typically ionized by electrospray techniques (ESI), their charge state can easily lie in the range 30-60 or exceed 60. Such high charges produce a peak with considerable signal-to-noise ratio (S/N). The root-mean-square error of the centroid mass determined for such a peak is much smaller than the width of the peak contributing to the accuracy of the mass position determination (see A. A. Makarov, E. Denisov, O. Lange, S. Horning. "Dynamic Range of Mass Accuracy in LTQ Orbitrap Hybrid Mass Spectrometer", *J. Am. Soc. Mass Spectrom.*, v. 17 (7), p. 977-982 (2006)). Accordingly, the ions are preferably multiply charged ions. More preferably, the charge state of the multiply charged ions is, in order of increasing preference, 20 or more, 30 or more, 30 to 80, or 40 to 80. The invention is particularly useful when the ions are multiply charged proteins, e.g. antibodies.

It is important to operate the mass spectrometer under conditions where there is a relatively low probability that a peak appears in a single mass spectrum that is a combined signal from ions of different mass. This can be achieved by adjusting the number of ions being simultaneously analysed in the mass spectrometer until the probability of multiple different ions being present within a given mass range in any single scan or spectrum acquisition is sufficiently low, i.e. below a threshold, and yet still enough to enable efficient detection of individual ions. Preferably, the probability is such that the number of peaks in a single spectrum due to two or more individual ions is 50% or less of the number of peaks due to one individual ion, more preferably 25% or less and most preferably 10% or less. Generally, if probability of detecting any signal in a given mass peak is P (P<1), then probability of detecting just one individual ion would be P/(1+P) and two or more individual ions would be P*P/(1+P), i.e. P times the probability of the former. So the values 50%, 25% and 10% above correspond to P=0.5, 0.25, 0.1. It should be noted that for a distribution of overlapping isotopes, this relates to the probability for an individual ion to appear within the window of dM and hence usually covers 2-3 neighbouring isotopes. This allows for a simple criteria for adjusting intensity while acquiring survey spectra. For a better compromise between peak resolution and acquisition time, it is preferable to keep P for the most intense peak below 0.5 but above 0.2. A peak being due to two or more individual ions typically means it has doubled intensity (where the ions are of same m/z) or exhibits peak interference (where the ions are of different m/z). Here doubled intensity means approximately double the intensity compared to the intensity of most of the peaks which are due to individual ions. Expressed conversely, preferably at least 50% of peaks in a single acquired mass spectrum are due to individual ions, more preferably at least 75% of peaks in a single acquired mass spectrum are due to individual ions and most preferably at least 90% of peaks in a single acquired mass spectrum are due to individual ions. In many cases, for large molecular ions produced by electrospray for example, ions are distributed across a wide range of charge states. For a typical example, charge states of intact antibodies could span over the range 40 to 80, each charge state containing several modifications, each containing >50 isotopes, each isotope carrying the number of charges corresponding to the charge state. As the amount of charge injected into a mass spectrometer with image current detection such as an FTMS spectrometer is typically below 0.1 picoCoulomb, this charge splits between a few thousand peaks leaving not more than a few individual multiply charged ions per peak. Therefore in such case it is sufficient to operate the spectrometer at a capacity just a few times lower than the maximum load.

The invention preferably comprises an ion signal or peak intensity optimisation step before acquiring the plurality of mass spectra in order to establish the conditions wherein most of the peaks in the spectra are due to individual ions or the probability of simultaneously detecting in a single spectrum any two ions giving rise to overlapping peaks in the m/z domain is significantly lower than the probability of detecting either of the two ions alone. This optimisation step may comprise the following steps:
  acquiring a survey spectrum;
  checking the peak or ion signal intensity in the survey spectrum;
  adjusting the peak or ion signal intensity if the peak or ion signal intensity in the survey spectrum is not within a determined limit;
  repeating steps i) to iii) until the peak or ion signal intensity in the survey spectrum is within the determined limit.

The determined limit is a peak or ion signal intensity such that most of the peaks in the spectra are due to individual ions or the probability of simultaneously detecting in a single spectrum any two ions giving rise to overlapping peaks in the m/z domain is significantly lower than the probability of detecting either of the two ions alone.

In the present invention, it is not required that there be strictly no overlapping peaks, rather it is sufficient that peaks either do not overlap or seldom do so. If the occurrence of overlapping peaks is sufficiently seldom then the resolving power in the final histogram may not be significantly affected and can be managed. The occurrence of overlapping peaks is preferably treated in some way to reduce any adverse effect on the resolving power. In one approach, overlapping peaks may be simply ignored in the centroid determination step, i.e. centroids are not determined for such peaks. Alternatively, peak deconvolution methods (e.g. peak fitting with one, two, or more model peaks) could be used to identify and treat cases where a small number of peaks overlap or interfere with one another, e.g. by resolving the overlapping peaks. After resolving the peaks to a satisfactory level, their centroids may be determined and counted in the histogram.

To maximize signal-to-noise ratio and therefore the accuracy of centroid determination, it is preferable to acquire each mass spectrum for longer periods, e.g. 1-2 seconds. However, in practice, there is a danger that not all ions would survive for the entire length of detection in such cases. In fact, in some cases most of them would decay during the detection resulting in weakened peaks with lower S/N ratios and poor mass accuracy. Empirically, it has been found that such weakened peaks typically exhibit S/N less than 25-50% of S/N of non-decaying individual ions thereby enabling them to be identified by their S/N. This problem of decayed ions can be addressed by several methods. In one approach, the pressure in the mass spectrometer, i.e. the analyser in which the ions oscillate and are detected by image current detection, is preferably reduced as much as possible since the proportion of such decayed ions depends strongly on the mean free path between collisions, as well as on the ion energy, charge, etc. and becomes acceptably small at the pressures of $<10^{-10}$ mbar typically achievable in an Orbitrap™ analyzer for example. Accordingly, preferably the pressure inside the spectrometer is $5*10^{-11}$ mbar or less. Counting of a sufficiently small number of decayed ions is acceptable in the method. Another approach to dealing with the decayed ions is that peaks with reduced S/N (i.e. as identified by a S/N below a determined threshold), are not used to provide centroids for the histogram.

Typically, in sufficiently low pressure conditions where decay is not a significant factor, the peaks may only need to be verified for occurrences of peak interference or doubled intensity (e.g. in substantially the same way as it is done in time of flight mass spectrometry) and after making corrections to such occurrences the histogram count is incremented by 0, 1 or 2 for the given mass positions. Preferably, only integers of centroids are used for the accumulation in the histogram, as each peak actually really accounts for an individual ion or perhaps two of the same ions. For instance, a count of 1 is added to the histogram where a peak (hence centroid) is due to an individual ion and a count of 2 (i.e. double the count) is added to the histogram where a peak is due to two of the same ions (as identified by an approximately doubled peak intensity compared to the intensity of the peaks due to individual ions). Alternatively, such peaks are discarded to avoid a chance of two ions coming not from the same but from neighbouring isotopic peaks. In other words, an upper limit on S/N could be beneficial. Most peaks are, however, due to individual ions with typically only a small minority due to two ions. Where a centroid is not determined and/or not used for generating the histogram, e.g. where it occurs with a peak interference, then the count for the histogram in that case is zero (0).

Herein, the term histogram means an occurrence distribution of the centroids. Thus the term means a generalised histogram and therefore includes histograms consisting of a series of data groups as described above, but also includes, e.g., a kernel density estimate (of which a normal histogram is a special case). Kernel density estimates are described, for example, at http://en.wikipedia.org/w/index.php?title=Kernel_density_estimation&oldid=389025950. The histogram is thus preferably a distribution from the plurality of spectra representing approximately the number of times (i.e. occurrences) that a centroid is counted, e.g. representing for each data group of the histogram approximately the number of times (i.e. occurrences) that a centroid is counted which falls into a data group of the histogram. The histogram therefore approximates to a sum of the centroids from the plurality of spectra. The data groups which the histogram is divided into need not be adjacent data bins but, as described above, the data groups may be adjacent or spaced apart and may be of flexible or regular width. The histogram is not limited by any particular graphical representation and may therefore be graphically represented in any number of ways, e.g. bar chart, scatter chart etc. or may be non-graphically represented, e.g. in numerical form such as in a table. The histogram preferably represents a quantized count of the centroids. Since the acquired mass spectra contain peaks mostly from individual ions (due to low ion population in the spectrometer) and occasionally from two of the same ions, the intensity of the peaks in the acquired spectra are typically quantized (i.e. they have a quantized S/N), wherein detection of an individual ion gives a peak in a spectrum with a S/N ratio of approximately x and detection of two ions simultaneously gives a peak in a spectrum with a S/N ratio of approximately 2x and so on. Where a peak is due to the detection of two ions simultaneously a count of two centroids may be contributed to the histogram or, alternatively, a count of zero is used so as to discard such peaks to avoid a chance of two ions coming not from the same but from neighbouring isotopic peaks. Ions which have undergone decay or fragmentation during the acquisition period for the mass spectrum typically give a peak which does not have a quantized S/N and as such those peaks can be detected and, if necessary, discarded from the count in the histogram.

When valid or accurate intensity information is required the ion statistics should be considered, e.g. to predict the number of spectra required for the histogram to be a representation of the real mass spectrum of sufficient accuracy, for example according to the statistical reasoning in U.S. Pat. No. 7,109,474.

It will be appreciated that the steps of the invention may be varied. For example, in some embodiments some or all of the plurality of mass spectra may be acquired before the centroids for those spectra are determined. In other embodiments, the centroids may be determined continuously as each spectrum is acquired, i.e. the centroids of a spectrum are determined before, or at the same time as, the next spectrum is acquired.

Calibration methods are known in the art and are preferably used in the present invention. Internal calibration and/or external calibration may be used, preferably internal calibration. It is preferable to use an internal calibrant to avoid any broadening of the peak due to the mass drift during the acquisition. Preferably, a pre-determined number of internal calibrant ions may be added to the analyte ions. In embodiments of the invention using Harmonic potential-FTMS a pre-determined number of internal calibrant ions may be added to the analyte ions using multiple fills of a C-trap, as described for example in WO 2006/129083.

The method preferably further comprises a step of outputting the histogram (composite mass spectrum), and/or any post-processed mass spectrum computed therefrom and/or any selected data or information obtained therefrom, e.g. using a video display unit (VDU) and/or printer.

The acquired and/or processed data, e.g. the acquired transients, acquired mass spectra, the histogram/composite mass spectrum etc., may be transferred to a data system, i.e. a mass data storage system or memory, e.g. magnetic storage such as hard disk drives, tape and the like, or optical discs, which it will be appreciated can store a large number of such spectra. The mass spectra held by the data system may be accessed by other programs, e.g. to allow for spectra output such as display, spectra manipulation and/or further processing of the spectra by computer programs at a subsequent time.

The mass spectrometer preferably comprises an ion source for producing ions. Any known and suitable ion source in the art of mass spectrometry may be used. Examples of suitable ion sources include, without limitation, ion sources which produce ions using electrospray ionisation (ESI), laser desorption, matrix assisted laser desorption ionisation (MALDI), or atmospheric pressure ionisation (API) such as Laserspray as well as others which are known in the art. An ESI source is a preferred method of ionisation, especially for proteins (e.g. antibodies etc.). The method of the present invention is especially applicable to the mass analysis of multiply charged ions, especially those with high charge states, such as produced by the ESI technique.

The ions produced in the ion source may be injected into the mass analyser by an ion injection device, preferably a pulsed ion injection device which injects a short packet of ions into the analyser. An example of a suitable ion injection device is a curved linear trap (C-trap) in the case of injection into the Orbitrap™ mass spectrometer, as described for example in WO 2008/081334.

The ions produced by the ion source may be transferred by well known methods and injection devices to a mass analyser, in which the ions are forced to oscillate and which separates the ions according to mass-to-charge ratio (m/z). The mass spectrometer thus also comprises a mass analyser for receiving ions from the ion source. Any suitable mass analyser known in the art of image current detection mass spectrometry may be used. Preferably, an FTMS analyser using image current detection is used. Examples of suitable mass analysers include FT-ICR mass analysers and ion traps that measure the frequency of ion oscillation induced by a potential that varies harmonically in one direction (harmonic potential-FTMS) such as the Orbitrap™ mass analyser for example. Other examples of such traps for use with the present invention may include traps which can be described by the Cassinian equation as described in C. Köster, Int. J. Mass Spectrom. Volume 287, Issues 1-3, pages 114-118 (2009) or in WO2009/001909.

The mass analyser may be used as part of a hybrid mass spectrometry system employing two or more mass analysers as in tandem ($MS^2$) and higher stage ($MS^n$) mass spectrometry and/or the mass spectrometer may be a hybrid mass spectrometer which comprises two or more different types of mass analysers, e.g. a Linear trap-FTMS mass spectrometer, such as the LTQ Orbitrap™ or LTQ FT™ ranges of mass spectrometers from Thermo Fisher Scientific. It will be appreciated therefore that the invention is applicable to known configurations of mass spectrometers including tandem mass spectrometers (MS/MS) and mass spectrometers having multiple stages of mass processing ($MS^n$).

Additional components such as collision cells may be employed to provide the capability to fragment ions prior to mass analysis by the mass analyser.

The ions separated according to mass-to-charge ratio (m/z) are detected by an image current detection system. Image current detection systems are well known in the art for FTMS and may be employed in the present invention for example.

It will be appreciated that the various stages of the mass spectrometer of ion source, injection device, mass analyser(s), and detection system, as well as optional stages such as, e.g., collision cells, may be connected together by ion optical components, as known in the art, e.g. using one or more of ion guides, lenses, deflectors, apertures etc.

The mass spectrometer may be coupled to other analytical devices as known in the art, e.g. it be coupled to a chromatographic system (e.g. LC-MS or GC-MS) or an ion mobility spectrometer (i.e. IMS-MS) and so on.

The mathematical steps of the invention are performed by a data processor which means an electronic device for processing data and the term encompasses one or more individual data processors. The data processor may be either programmable (i.e. having one or more programmable elements) or non-programmable (i.e. not having a programmable element) or have both one or more programmable elements and one or more non-programmable elements. The data processor may be a general purpose electronic processor (i.e. capable of performing other steps than the steps described herein) or a dedicated electronic processor (i.e. dedicated to the steps described herein). Examples of data processor include, without limitation, a computer or dedicated electronic processor, e.g. DSP, ASIC, FPGA, GPU and the like. A preferred data processor for the present invention comprises a computer. Accordingly, the steps of Fourier transforming the transient to obtain the mass spectra, and calculating the centroids (m/z-intensity pairs), and optionally any other processing of the spectra (e.g. to identify and deconvolute overlapping peaks and filter out centroids of low intensity, low S/N etc), and indeed any steps of the invention comprising running of an algorithm or performing a calculation, may be implemented in computer software. Alternatively such steps may be performed using specifically designed hardware to facilitate the processing of data, e.g. a dedicated electronic processor which does not use computer software. Preferably such steps of the present invention are performed with the aid of a computer running computer software. In general, any steps of the present invention which involve processing data are preferably implemented in computer software. The invention may therefore be implemented, e.g. partially, in computer software.

BRIEF DESCRIPTION OF THE DRAWINGS

In order to more fully understand the invention, various non-limiting examples of the invention will now be described with reference to the accompanying Figures in which.

DETAILED DESCRIPTION

Figure 1:
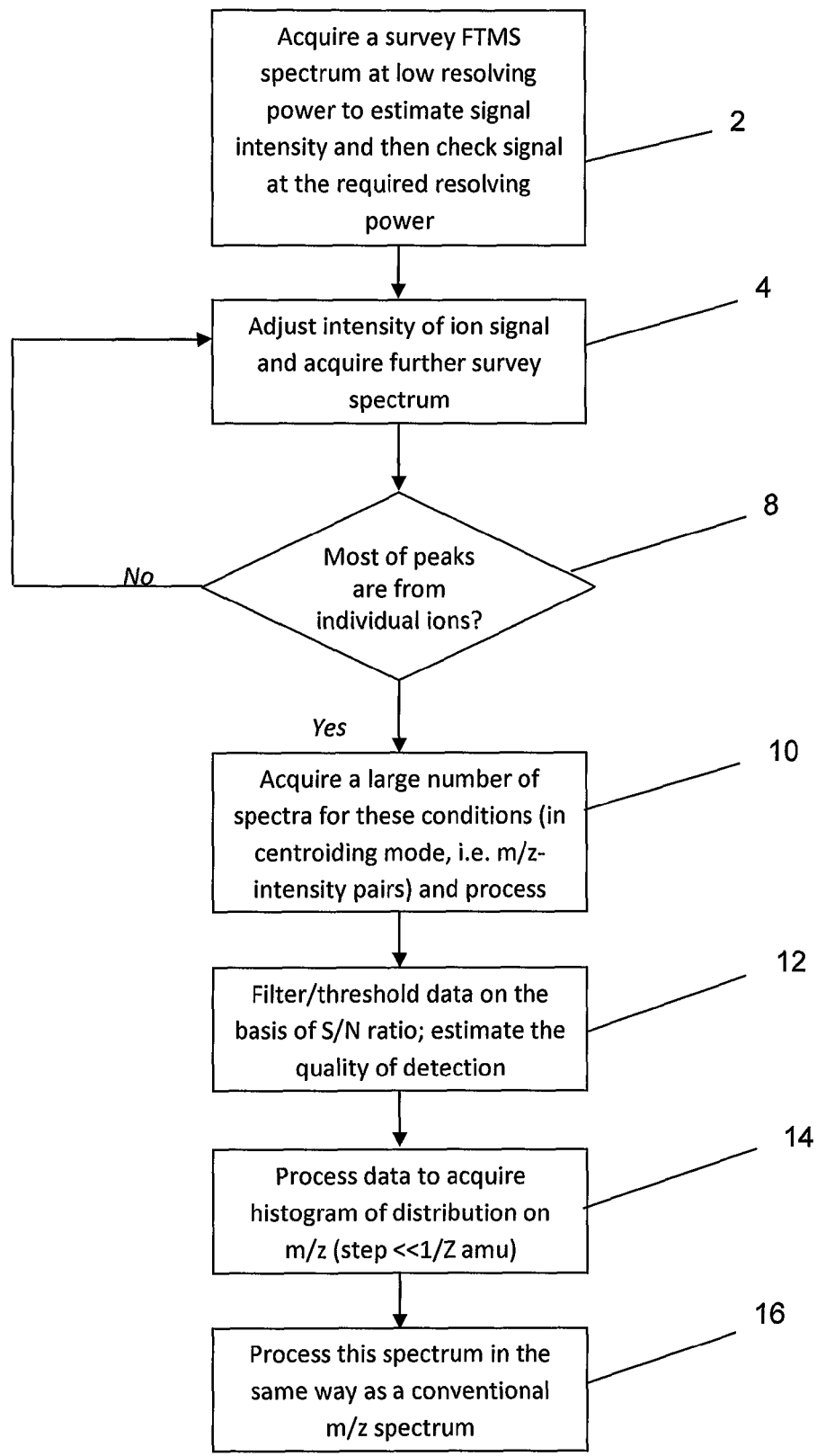
FIG. 1 shows schematically a flow chart of an embodiment incorporating a method according to the present invention.

The method shown schematically in FIG. 1 comprises steps 2 to 8 which are steps for optimising the ion signal or peak intensity for carrying out the method according to the present invention. Referring to FIG. 1 in a preliminary step 2 a first mass spectrum is acquired from an FT mass spectrometer, such as an FT-ICR or Orbitrap™ spectrometer for example, using image current detection. The mass spectrum is a spectrum obtained after Fourier transformation of the transient generated from image current detection of the oscillating ions in the spectrometer. This first spectrum acts as a first survey spectrum and, for example, may possibly be acquired using normal acquisition parameters of the spectrometer, e.g. with relatively high ion load. Alternatively, if the acquisition parameters for running the method of the present invention are approximately known (e.g. from a previous experiment), it may save time to acquire the first survey spectrum with the approximately correct parameters for the present invention so that the number of survey spectra and hence time required for optimization of the parameters is reduced. The ion signal or peak intensities in the first survey spectrum are then checked to see if they are too high (or too low). Preferably, at least the first survey spectrum may be acquired at a low resolving power to estimate the signal intensity and then the acquisition is repeated as described below in steps 4 and 8 at the required resolving power to check the signal. After checking the signal intensity of the first survey spectrum, the peak or ion signal intensity is adjusted in step 4 by adjusting the number of ions injected into the spectrometer to try to bring the peak or ion signal intensity in the survey spectrum below the determined limit or threshold. The determined limit or threshold is a peak or ion signal intensity such that most of the peaks in the spectra are due to individual ions or the probability of simultaneously detecting in a single spectrum any two ions giving rise to overlapping peaks in the m/z domain is significantly lower than the probability of detecting either of the two ions alone. Typically, the number of ions in the spectrometer is adjusted so that the probability of detecting any signal for a given mass peak is P (where P<1), then probability of detecting just one individual ion is P/(1+P) and two or more individual ions is P*P/(1+P), i.e. P times the probability of the former. This allows for a simple criteria for adjusting intensity while acquiring survey spectra. Typically, the ion number is adjusted to keep P for the most intense peak below 0.5 but above 0.2 as a good trade-off between peak resolution and acquisition time. After adjusting (typically reducing) the ion signal in step 4 by adjusting the number of ions in the spectrometer a further survey spectrum is acquired, followed by checking again in step 8 whether the ion signal or peak intensities in the survey spectrum are within the determined limit. If the ion signal or peak intensities in the survey spectrum are still not within the determined limit such that most of the peaks are due to individual ions, then the method repeats steps 4 and 8 until eventually the ion signal or peak intensities in the survey spectrum is within the determined limit and the necessary conditions for acquiring spectra for the performance of the present invention have been established, i.e. most of the peaks are due to individual ions.

This iterative adjustment of the number of ions could, for example, be done using a binary search-type process, calculation based on the observed intensities and/or ion statistics or any other method that quickly leads to the desired number of ions.

A binary search-type of optimisation could be used in this case in which an ion time or "Automatic Gain Control (AGC)-target" would e.g. be halved if too many ions are present or doubled if not enough ions are present and then similarly the value halfway between the last two tests or half the value would be used. Due to the nature of the problem it may be more efficient to do the calculations based on log (target). The criterion would be met when the desired number of peaks show the desired height quantization corresponding to one individual ion.

A calculation based on observed intensities comprises conducting a calibration and connecting a certain S/N with a certain number of charges. When the charge is known or can be inferred from the data, which is frequently possible and methods for doing this are known to those skilled in the art, then the correct target (or ion time) may be directly determined from the measured peak height. For example: if a S/N per charge of 0.3 is assumed, then if a signal is measured to have height (intensity) 100 and charge of 12, it should have intensity 3.6*Noise (12*0.3) so to get down to one individual ion, the ion time (or target) should be divided by approx. 28. Another iteration may be necessary when there is not strictly linearly behaviour.

Use may be made of ion statistics but this will usually be combined with one of the previous methods. From ion statistics it is possible to tell that the (scan to scan) variation of consecutive measurements (for the same target/ionization time) is (proportional to) SQRT (number of ions). For a single ion the variance is equal to the intensity. So a better target can be determined from the current target by multiplying it with Q=variance(signal)/signal.

A standard Automatic Gain Control (AGC) software as used already with FTMS such as the Orbitrap™ could be modified to recognize the statistical ion distributions and optimize for a maximum total number of ions while maintaining ion numbers sufficiently low to keep the interference rate between peaks below any desired threshold. Typical target values for the number of ions over mass interval $\Delta M$ in a.m.u. for a charge state Z would be below $Z*\Delta M$, preferably between 0.1 and 0.5 of $Z*\Delta M$. Typically, $Z*\Delta M$ should not exceed $10^5$-$10^6$ to avoid space-charge effects in FTMS.

In step 10, a large number of spectra are acquired using the numbers of ions in the spectrometer as previously optimised in steps 2 to 8. Spectra are acquired until the amount of information gathered is sufficient. The number of spectra acquired could be just a pre-determined number of spectra which is known to be sufficient (e.g. 100, 1000, or 10000 spectra), or e.g. until a particular selected peak (e.g. the most abundant peak) has been recorded for a certain number of ions (e.g. 10, 50, 100 ions) or until its accumulated intensity reaches a certain level, or any other desired criteria is fulfilled. Typically, several thousand spectra may be acquired for high resolving powers. In the embodiment shown, the spectra are acquired using a centroiding mode in which the centroids of all or selected peaks in the spectra are determined, along with intensity data for the centroids. The spectra thus obtained comprise m/z-intensity pairs and are hereafter termed centroid spectra. There exist numerous suitable centroiding algorithms well known in the art to obtain the centroids of the peaks. The centroid is the mathematically determined position of a peak, here the mass, m/z or frequency, typically determined by fit of a model peak to the measured data points, fit of a parabola to the top 3 points of a peak (i.e. take the topmost point and it's two neighbours and then calculate the apex of the parabola that goes through these 3 points), by use of quadratic forms (e.g. Quinn's estimator) or any other mathematical method. Further methods for determining centroids are given for example in Jacobsen, E., On Local Interpolation of DFT Outputs (only published on-line: http://www.ericjacobsen.org/fe.htm), and Serreqi, A. & Comisarow, M. B., Frequency Interpolation of Discrete, Apodized, Magnitude Lineshapes, Applied Spectroscopy, 1987, 41, 288-295. Calculation of the centroids may be done "on-the-fly" using existing fast processors. Alternatively, the full data set of spectra may be transferred to memory and the centroid determination performed subsequently by the spectrometer computer, although that is less preferred because disk space requirements increase by several orders of magnitude.

The acquired spectra may be processed individually e.g. to identify overlapping (interfering) peaks, mass correcting the peak positions using a calibrant (e.g. internal standard), and/or normalisation where all intensities are set to 1 etc.

An algorithm to process the spectra and identify overlapping peaks, which have reduced resolution, is preferably applied. Algorithms to identify peaks which overlap are again well known in the art. Overlapping peaks may be characterised, for example, by an overbroad peak width or overly high intensity. Many centroiding algorithms (including the "parabola method" described above) also provide the peakwidth, so that a convenient point to identify overlapping or overbroad peaks is with the centroiding in step 10. Alternatively, the detection of overlapping or overbroad peaks may be performed after centroiding, e.g. together with the histogram build-up. The occurrence of overlapping peaks is then treated, e.g. by either not using overlapping peaks for further processing (discarding the overlapping peaks or even discarding the spectrum containing them) or by applying a peak deconvolution method to resolve the peaks mathematically to a satisfactory level if that is possible. Of course, only the former "discarding" treatment is possible for overlapping peaks or defective peaks once the original data are discarded, e.g. in the case of centroiding on-the-fly where only the data from centroiding is kept. Peak deconvolution methods require the original data to be kept. If overlapping peaks can be satisfactorily resolved by deconvolution methods then their centroids may be determined and used for further processing. If overlapping peaks cannot be satisfactorily resolved by deconvolution methods then their centroids may be discarded.

The centroiding process and other data processing are performed in this case by a computer. All of the centroid data, i.e. all of the m/z-intensity pairs, are stored in memory. The full spectral data (transients and/or transformed mass spectra) may also optionally be stored in memory in case they need to be used again in the future but the latter is clearly at the expense of considerable memory space.

After obtaining the centroid spectra in the form of m/z-intensity pairs, and after processing the spectra as described above, a step 12 is preferably performed for filtering the centroid spectra to remove poor quality peaks. One or more filters may be applied to the centroid spectra. A preferred filter is a signal-to-noise (S/N) filter which compares the centroid spectra to an S/N threshold and only allows centroids to be used for further processing which have intensity at or above the threshold. Only individual ions are detected with a peak having S/N substantially higher than 1, preferably 3 or higher, more preferably 5 or higher and more preferably 10 or higher. The threshold is preferably the S/N which an un-decayed individual ion has in the spectrum. The un-decayed individual ions have an S/N which is approximately the same and quantised. The method may therefore preferably only use centroids which have the quantised S/N. In this way, peaks due to ions which have decayed during the acquisition of the spectra and which have significantly reduced S/N (and have non-quantised S/N) and correspondingly poor resolution are filtered out. In cases, where the problem of decayed ions is insignificant, the filter on S/N step may be omitted, which may be the case, for example, for relatively short acquisition times and/or in cases where the pressure in the spectrometer is sufficiently low to avoid significant decay problems. The S/N threshold for the peaks is sufficiently high so that high mass accuracy is achieved, i.e. the variation of the centroid for a peak from the plurality of mass spectra is significantly lower than its full-width at half-maximum dM in the m/z domain. The full-width at half-maximum dM of a peak in the m/z domain in this context means the average full-width at half-maximum of the peak from the plurality of acquired mass spectra. The variation of the centroid of a peak from the plurality of acquired mass spectra herein means the extent to which the centroid value varies across the plurality of spectra (i.e. difference from the highest to lowest determined value of the centroid).

In the next step 14, the centroid spectra are processed by summing the centroids of selected peaks of interest or, if desired, of all peaks in the spectra, thereby generating a histogram of the centroids against m/z. This histogram then is a composite mass spectrum of all the acquired mass spectra which contain peaks mostly due to individual ions and represents the mass spectrum of the selected ions of interest since a statistically significant number of centroid spectra are acquired.

Grouping or binning of the summed up centroids in the histogram can be done automatically or by selection of a mass tolerance (either from calibration data or from a user setting). The data group width of the histogram is less than the data group width of the acquired mass spectra in the m/z domain and usually is at most 0.5 times the data group width of the acquired mass spectra in the m/z domain. The group width or m/z step width in the histogram is preferably less than or equal to ($\leq$) 1/z atomic mass units (amu), where z is the expected charge state of the ion, and preferably is much less than ($<<$) 1/z amu. In the preferred example, the data group width of the histogram is 0.1 times the data group width of the acquired mass spectra in the m/z domain. The histogram spectrum thus provides a mass spectrum which has significantly improved resolving power compared to the individual acquired spectra.

Figure 2:
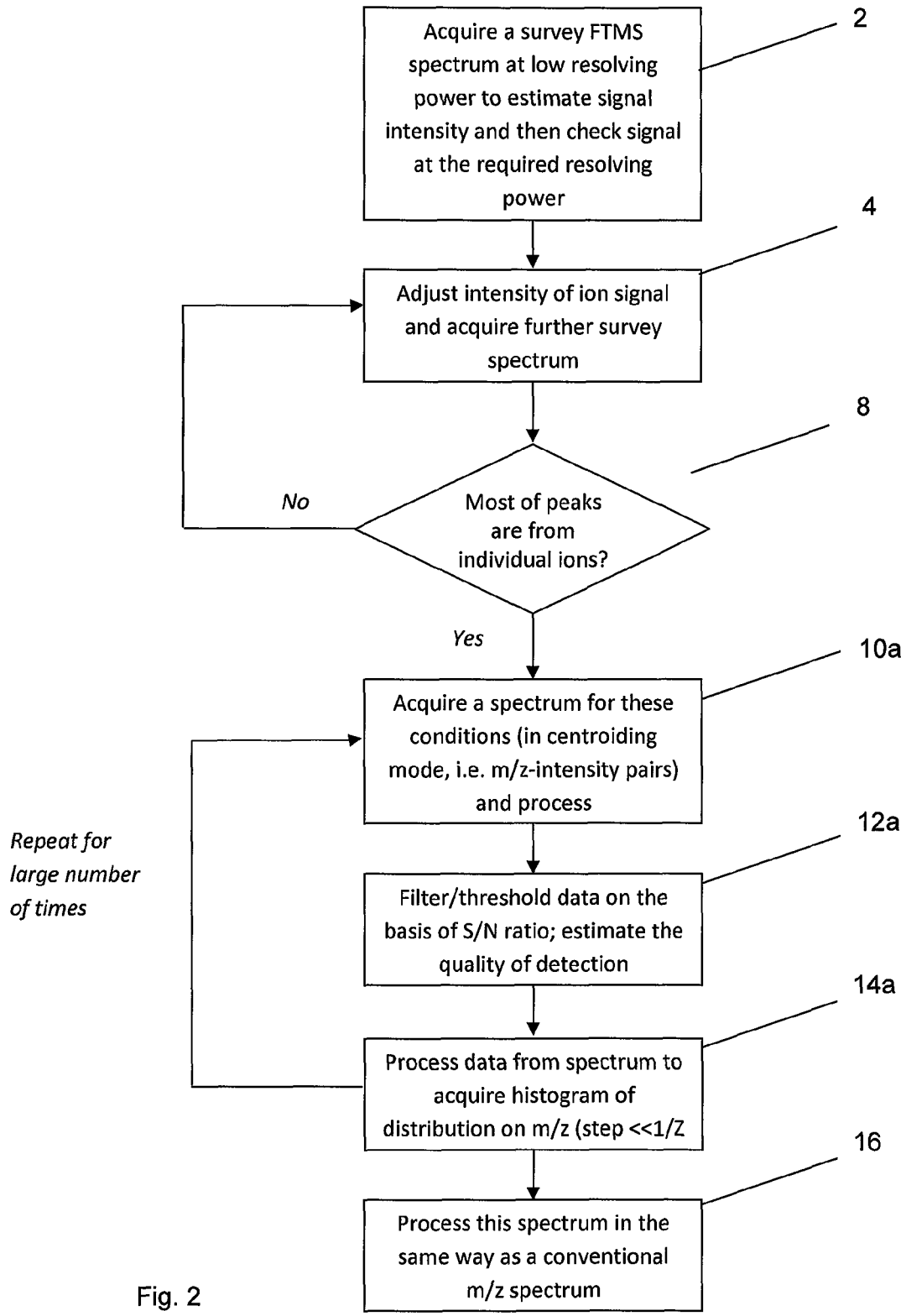
FIG. 2 shows schematically a flow chart of a further embodiment incorporating a method according to the present invention.

It will be appreciated that the histogram need not be generated only after all of the centroid spectra have been acquired but, alternatively, the centroids may be added continuously to the data groups of the histogram as each spectra is acquired, i.e. to form the histogram continuously. Such an embodiment is shown in FIG. 2, wherein the steps 2, 4 and 8 are the same as for the embodiment shown in FIG. 1 but step 10a comprises acquiring a single spectrum of the mostly individual ions and then optionally processing it as described above for overlapping peaks etc. before step 12a comprises optionally filtering on the S/N as described above, and before adding the centroids from the spectrum to the histogram at step 14a. Then the process steps 10a, 12a, 14a are repeated a large number of times with the centroids being added to the histogram at step 14a each time before acquiring the next spectrum at step 10a, thereby compiling the histogram continuously. It will be appreciated that in a further variation of the FIG. 2 embodiment, the next spectrum may be acquired in step 10a whilst the previous spectrum is still being processed in steps 10a, 12a and 14a.

The resulting composite mass spectrum which is provided by the histogram may then be used just like a normal mass spectrum for post processing and analysis (step 16 in FIGS. 1 and 2), e.g. deconvolution processing by software in order to estimate monoisotopic mass of the protein (using for example a maximum entropy method) and its modified forms, quantitative analysis etc. The centroid histogram is compiled by computer and is stored in memory for subsequent processing and analysis. Output of the histogram and any analysis and results derived therefrom is made to a VDU and/or hard copy.

When the charge states are known, ions from different charge states could be summed into a single histogram, reducing the number of spectra required to reach a given intensity accuracy. This is typically a part of a normal deconvolution to restore monoisotopic mass. Several methods may be used to ascertain charge states, such as the following:

a) the charge state is directly determined from m/z, for example when an approximate mass M of the protein is known then using M=z*m/z the charge can be calculated by dividing M by m;

b) the charge can be directly inferred from the isotope spacing. If peaks appear a fraction of an m/z unit apart, the charge is 1/fraction (e.g. for charge=3 the spacing between isotopes is ⅓ m/z units). Unfortunately this method of charge determination tends to work only when the invention may not be needed, because the isotopes are already resolved, unless isobaric resolution is desired for example;

c) some ionization methods may produce different charge states. For example electrospray creates a series of consecutive charge states (i.e. we get signals at . . . , m/(N−1), m/(N), m/(N+1), m/(N+2), . . . . The formula from b, can then be used to infer the charge state N from 3 neighbouring peaks, even when m is unknown and isotopes are not resolved by solving the two algebraic equations $$dm1 = m/(N-1) - m/(N)$$

$$dm2 = m/(N) - m/(N+1)$$

for N.

The reliability of this method can be improved by use of more mass distances. Further details are given in U.S. Pat. No. 5,581,080 for example. The method works best when resolution is low enough to give only the envelopes of the isotopic patterns.

In the methods of b) and c) when there are many of these peaks with different charges it may be possible to have the isotopes resolved at one charge state. The others can then easily be inferred using the above reasoning.

Figure 3A:
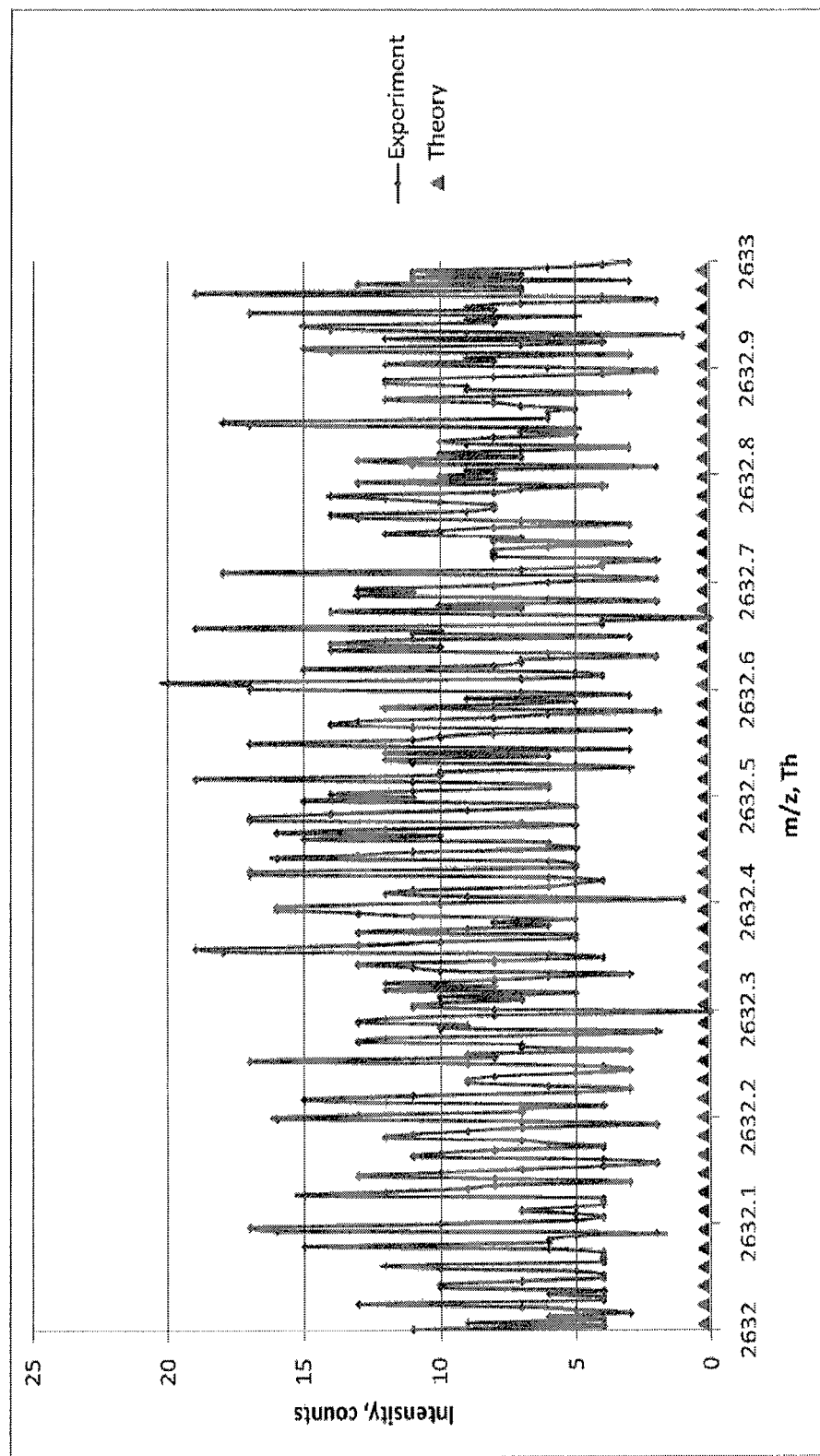
FIG. 3A shows a histogram mass spectrum obtained from measurements using the method of the present invention for an intact antibody IgG for a narrow m/z range.
Figure 3B:
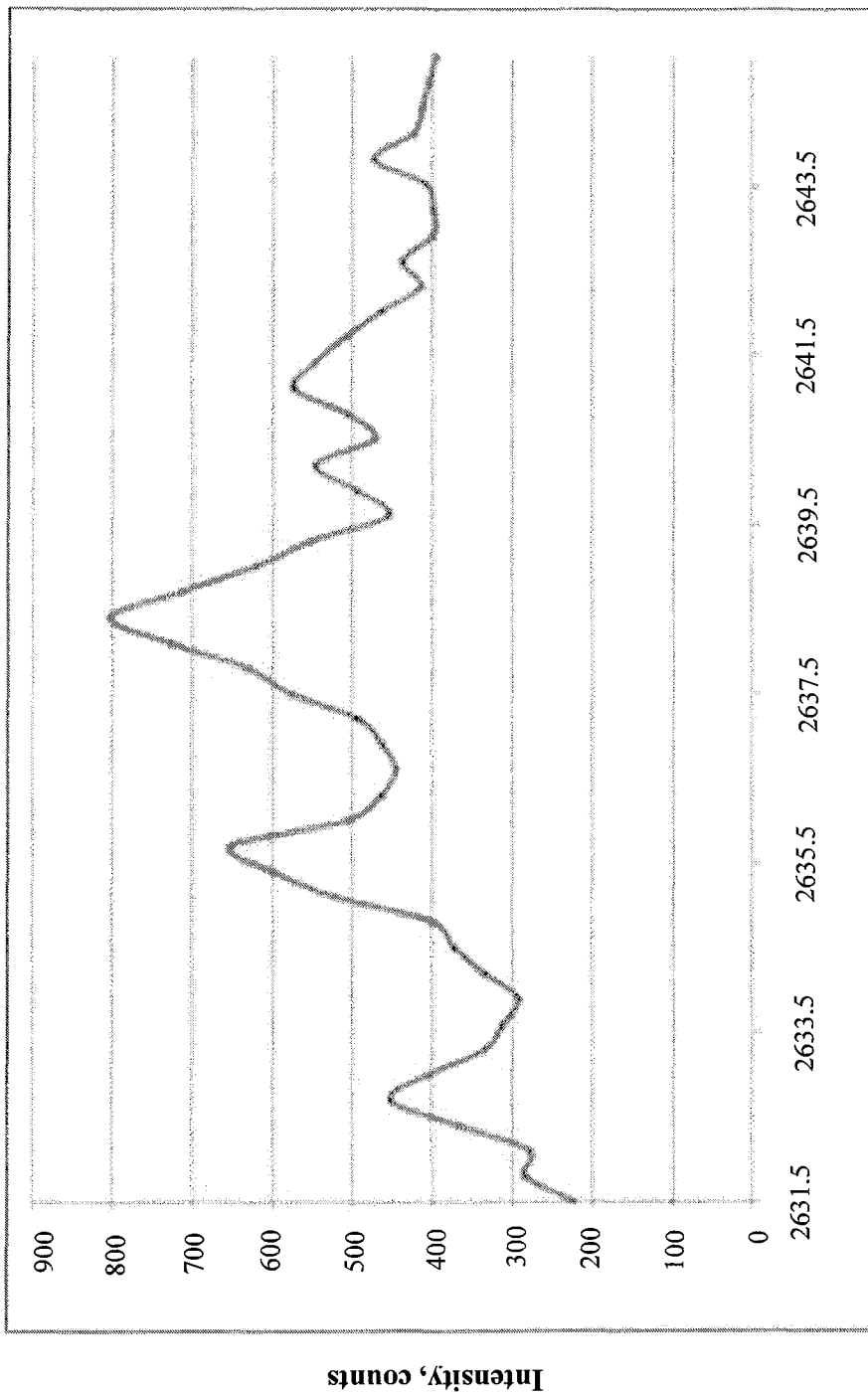
FIG. 3B shows the histogram of FIG. 3A for a broader mass range showing a smoothed envelope of isotopic distributions.

Referring to FIG. 3A, there is shown a histogram mass spectrum obtained from measurements using the method of the present invention showing peak positions and heights of isotopic peaks of an intact antibody IgG (MW 149994 Da, +47 charge) compared to the theoretically predicted positions (positions shown by the triangles). The measurements were carried out on an LTQ Orbitrap Velos mass spectrometer from Thermo Fisher Scientific with the resolving power set to 100,000 (corresponds to about 55,000 at the measured m/z of about 2640). The measured peak positions agree well with the theoretical positions. The isotopic pattern observed with this histogramming method of the invention would have required >250,000 "raw" resolving power (i.e. an almost 5-fold increase in resolving power in this case). Referring to FIG. 3B there is shown a smoothed envelope of isotopic distributions, within a broader mass range, including unmodified as well as glycosylated antibodies from which the spectrum in FIG. 3A is taken.

The working of the invention is further explained with reference to FIGS. 4 to 7. With regard to the ion load in the mass spectrometer to ensure most of the peaks are due to single ions, consider a theoretical substance of interest that produces 100 peaks of interest which are all of the same intensity (for true high mass ions the isotopic distribution approximately approaches this situation with increasing mass) and approximately equally spaced with a standard peak distance s. If peaks are considered to overlap or merge when they are less than about 5 s apart, then the probability that 2 peaks merge for an ion load of 2 ions is about 10%, meaning that an average ion load of 2 ions could be accepted. When two non-overlapping charge states are present with equal probabilities, the number of acceptable ions at the same time would already double again.

Figure 4:
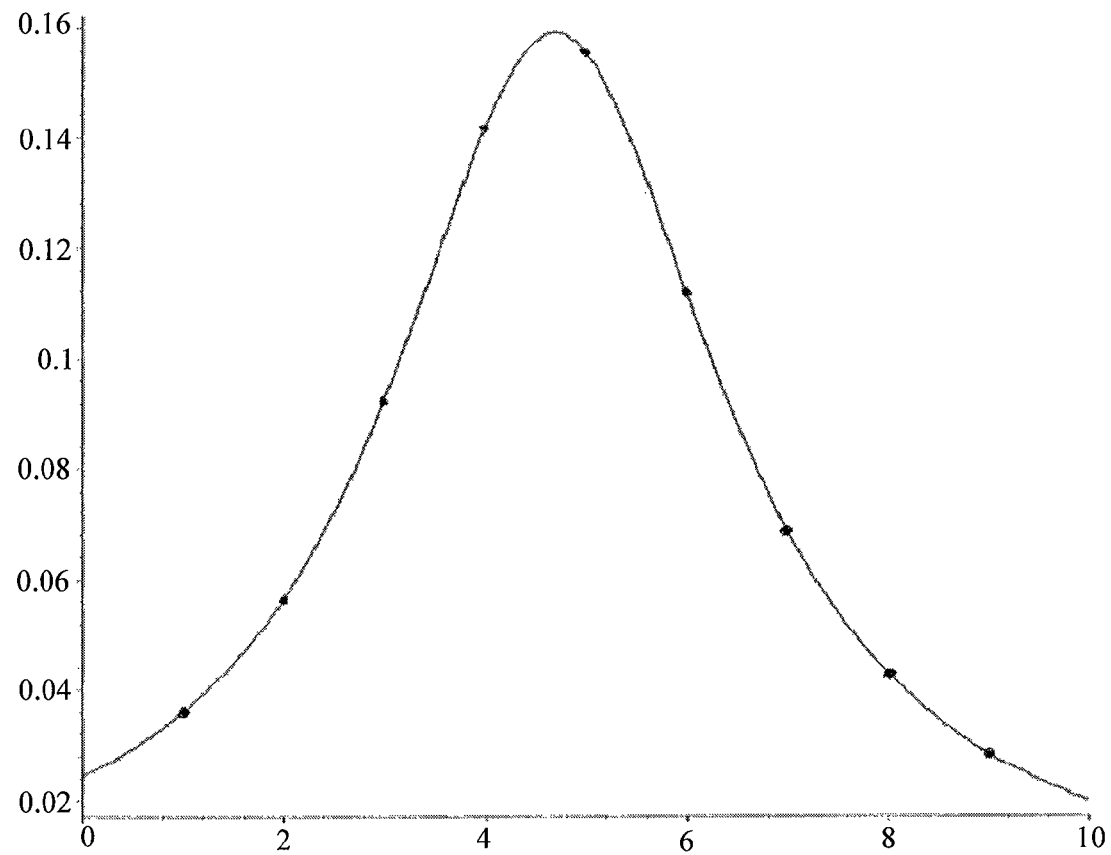
FIG. 4 shows a model peak represented by the curve and it's digital representation represented by the data point markers to illustrate the working of the present invention.
Figure 5:
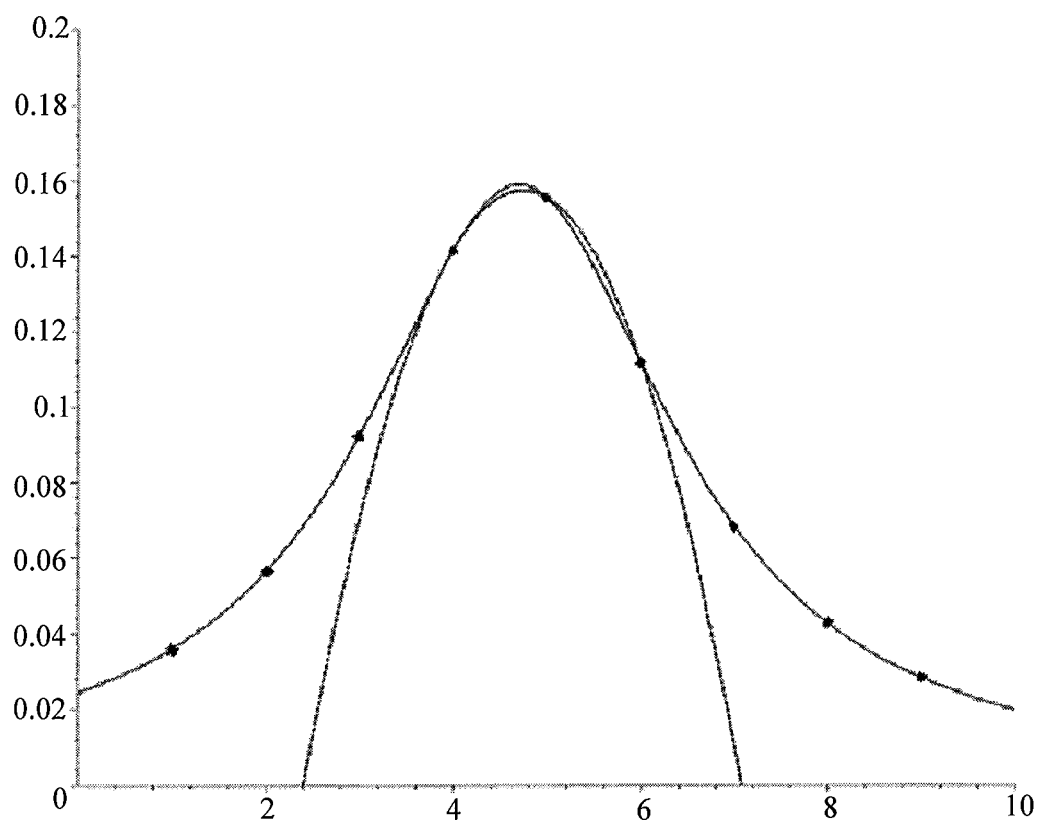
FIG. 5 shows a simple model peak in the form of a parabola fitted through the topmost data points of the peak of FIG. 4.
Figure 6:
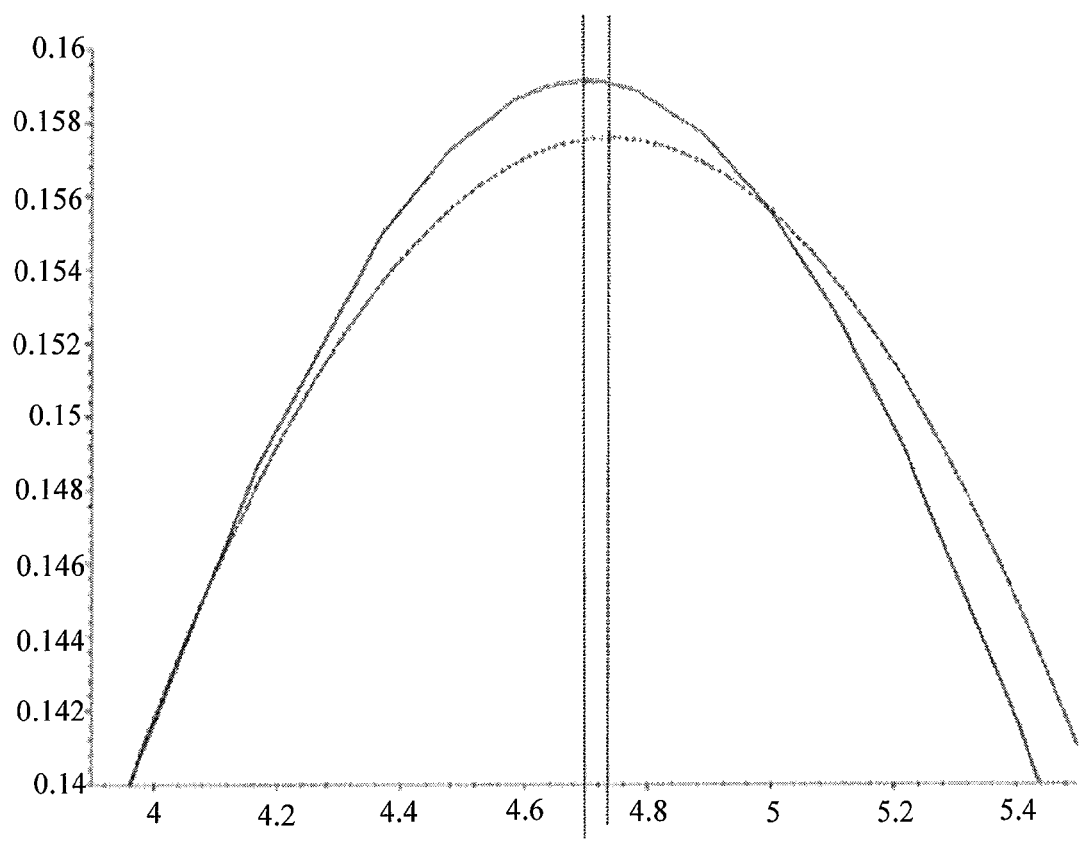
FIG. 6 shows a view on a zoomed-in scale of the FIG. 5 peak fitting.
Figure 7:
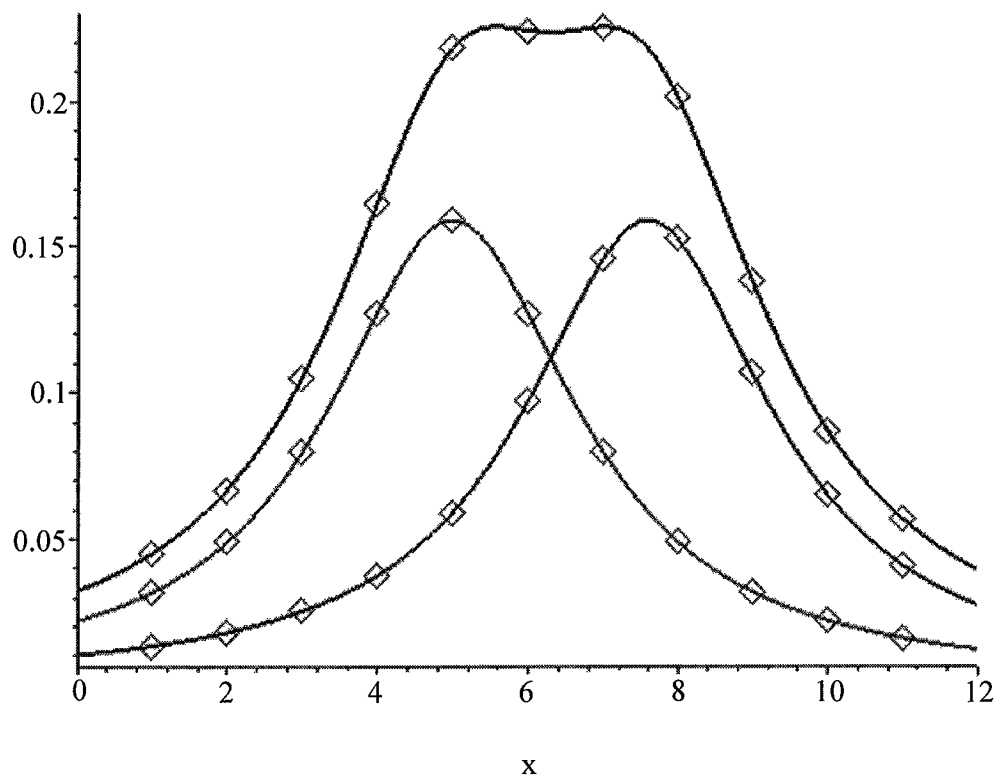
FIG. 7 shows an example of two model overlapping peaks which can readily be resolved using the method of present invention.

Referring to FIG. 4, there is shown a model peak, in this case Lorentzian peak, as represented by the curve and it's digital representation as represented by the data point markers. In this case, the data is grouped into regular width data bins. From a measurement only the data points of the digital representation are available for the data evaluation process. From these data points the exact peak position has to be determined by a centroiding method. The accuracy of this peak position (centroid) calculation is determined by the inherent accuracy of the fit procedure and the error (e.g. from noise) in the measurement of the data points. The position or centroid of the peak may, for example, be determined by fitting a quadratic form to the data points. For illustration, in FIG. 5 a simple model peak in the form of a parabola is fitted through the topmost three data points of the peak. Referring to FIG. 6, there is shown an expanded view of the FIG. 5 peak fitting (which is for visualization purposes chosen in an area of nearly worst case performance of the parabolic fit). The error in the determination of the maximum from the parabola (compared to the true centre position) is about 0.04 bin distances, i.e. less than 1/20 of a bin width. Whether a single peak in one spectrum and another peak in the next spectrum can be distinguished from one another depends on the ability to perform this (or a similar) level of precision of position determination. Peaks which are separated by more than 2 of these position determination errors may be considered different in position/mass/frequency. When there's no or negligible mass jitter in the measurement from one scan to another (as is typical for FTMS instruments like FT-ICR and an Orbitrap™) this estimation accuracy is typically around 0.1 bin distances or better, depending on the estimation method and the signal to noise levels (See Jacobsen, E. (EF Data Corporation) On Local interpolation of DFT Outputs (only published on-line), 2002. In contrast, when the peaks occur in the same spectrum, the distance for peaks to begin to be distinguishable is about 2 to 3 bin widths. FIG. 7 shows an example where two peaks are approximately 2.6 bin widths apart. From the acquired spectrum data points alone only a single maximum (approximately at bin 7) is found. Even though the curve from peak fitting shows a dip, the peaks cannot be told apart from the digitised data alone. Thus, these two peaks are for practical purposes indistinguishable. The invention instead measures these peaks in separate spectra due to individual ion measurement and with the high mass accuracy and precision of centroid determination, the peaks are readily resolvable. Limitations are ultimately imposed by noise which is the largest practical source of centroiding error.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language) provided herein, is intended merely to better illustrate the invention and does not indicate a limitation on the scope of the invention unless otherwise claimed. No language in the specification should be construed as indicating any non-claimed element as essential to the practice of the invention.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention claimed is:

1. A method of generating a mass spectrum, comprising:
   inducing oscillation of a plurality of ions within a spectrometer;
   measuring a plurality of transients of an image current induced on a detection electrode by the oscillation of the plurality of ions in the spectrometer;
   transforming the transients into a plurality of mass spectra wherein most peaks are due to detection of individual ions;
   using a processor for determining centroids of at least some of the peaks which are due to the individual ions and which have a sufficient signal-to-noise (S/N) ratio so that a variation of a centroid of each such peak from the plurality of mass spectra is less than 0.5 times the full-width at half-maximum, dM, of the peak in the m/z domain; and
   generating a histogram of the centroids determined from the plurality of mass spectra thereby forming a composite mass spectrum wherein the composite mass spectrum comprises peaks and the full-width at half-maximum, dMC, of these the peaks of the composite mass spectrum in the m/z domain is at least two times narrower than the full-width at half-maximum, dM, of the corresponding peaks in the plurality of mass spectra.

2. A method as claimed in claim 1 wherein the plurality of mass spectra are acquired with a mass precision of the peaks such that the variation of the centroids is narrower than a mass separation between adjacent peaks.

3. A method as claimed in claim 2 wherein the mass precision is at most 0.2 times the full-width at half-maximum, dM, in the plurality of mass spectra.

4. A method as claimed in claim 2 wherein the mass precision of the peaks in the plurality of mass spectra is 1 ppm or less.

5. A method as claimed in claim 1 wherein a mass accuracy of the peaks in the plurality of mass spectra is 5 ppm or less.

6. A method as claimed in claim 1 wherein the signal to noise ratio (S/N) of the peaks for which the centroids are determined is at least 2.

7. A method as claimed in claim 1 wherein the full-width at half-maximum dMC of the peaks in the m/z domain in the composite spectrum is at least 3 times narrower than the full-width at half-maximum dM of the corresponding peaks in the plurality of mass spectra.

8. A method as claimed in claim 2 wherein the centroids are collected in the histogram in data groups which are at least PO 2 times narrower in width than the full-width at half-maximum, dM.

9. A method as claimed in claim 1 wherein a data group width of the histogram is at least PO 2 times narrower than a data group width of the plurality of mass spectra in the m/z domain.

10. A method as claimed in claim 1 comprising acquiring a sufficient number of mass spectra such that the histogram of the centroids approximates to a real mass spectrum of the analyte.

11. A method as claimed in claim 1 wherein the ions are protein ions and/or multiply charged ions having a charge state in the range 30 to 80.

12. A method as claimed in claim 1 wherein the mass spectrometer is a Fourier transform mass spectrometer which is an FT-Ion Cyclotron Resonance mass spectrometer or a mass spectrometer which measures a frequency of oscillation of ions induced by an electrostatic potential which varies harmonically in one direction.

13. A method as claimed in claim 1 further comprising filtering out peaks in the plurality of mass spectra which have a S/N below a threshold.

14. A method as claimed in claim 1 further comprising identifying peaks in the plurality of mass spectra which have doubled intensity compared to most of the peaks and giving the centroid from such identified peaks double the count in the histogram or discarding them.

15. A method as claimed in claim 1 further comprising identifying overlapping peaks in the plurality of mass spectra, and discarding them or applying a deconvolution to such identified peaks to resolve them and determining the centroids of the peaks after resolving them.

16. A method as claimed in claim 1 further comprising optimising a peak intensity before transforming the plurality of mass spectra, the optimising comprising the steps of:
   a. acquiring a survey mass spectrum;
   b. checking the peak intensity in the survey mass spectrum;
   c. adjusting the peak intensity if the peak intensity in the survey mass spectrum is not within a determined limit; and
   repeating steps a) to c) until the peak intensity in the survey mass spectrum is within the determined limit.

* * * * *

UNITED STATES PATENT AND TRADEMARK OFFICE
CERTIFICATE OF CORRECTION

| | | |
|---|---|---|
| PATENT NO. | : 9,043,164 B2 | |
| APPLICATION NO. | : 13/278015 | |
| DATED | : May 26, 2015 | |
| INVENTOR(S) | : Alexander A. Makarov | |

It is certified that error appears in the above-identified patent and that said Letters Patent is hereby corrected as shown below:

Claims

Column 19, line 62, Claim 1,
replace "of these the peaks of the composite"
with --of the peaks of the composite--

Column 20, line 21, Claim 8,
replace "which are at least PO 2 times narrower"
with --which are at least 2 times narrower--

Column 20, line 25, Claim 9,
replace "is at least PO 2 times narrower"
with --is at least 2 times narrower--

Signed and Sealed this
Twenty-third Day of February, 2016

Michelle K. Lee
*Director of the United States Patent and Trademark Office*